United States Patent
Maitra

(10) Patent No.: US 8,871,507 B2
(45) Date of Patent: Oct. 28, 2014

(54) METHOD OF INHIBITING APOLIPOPROTEIN-E EXPRESSION COMPRISING ADMINISTERING A TRIARYLMETHYL AMINE COMPOUND

(71) Applicant: California State University Fresno, Fresno, CA (US)

(72) Inventor: Santanu Maitra, Clovis, CA (US)

(73) Assignees: California State University, Fresno, Fresno, CA (US); California State University, Fullerton, Fullerton, CA (US)

( * ) Notice: Subject to any disclaimer, the term of this patent is extended or adjusted under 35 U.S.C. 154(b) by 0 days.

(21) Appl. No.: 14/091,154

(22) Filed: Nov. 26, 2013

(65) Prior Publication Data
US 2014/0080209 A1    Mar. 20, 2014

Related U.S. Application Data

(62) Division of application No. 13/536,738, filed on Jun. 28, 2012, now Pat. No. 8,633,195.

(51) Int. Cl.
| | | |
|---|---|---|
| C12N 5/07 | (2010.01) |
| A61K 31/5375 | (2006.01) |
| A61K 31/135 | (2006.01) |
| A61K 31/495 | (2006.01) |
| C12N 5/09 | (2010.01) |
| C12N 5/071 | (2010.01) |
| C12N 5/079 | (2010.01) |
| A61K 31/40 | (2006.01) |
| A61K 31/4453 | (2006.01) |

(52) U.S. Cl.
CPC .......... *C12N 5/0693* (2013.01); *A61K 31/5375* (2013.01); *A61K 31/135* (2013.01); *A61K 31/495* (2013.01); *C12N 5/067* (2013.01); *C12N 5/0622* (2013.01); *A61K 31/40* (2013.01); *A61K 31/4453* (2013.01)
USPC ............................ 435/366; 435/368; 435/375

(58) Field of Classification Search
USPC ......................................... 435/366, 368, 375
See application file for complete search history.

(56) References Cited

PUBLICATIONS

Dhah et al. Synthesis, Characterization and Biological Screening of Apolipoprotein-E (apoE) Modulators based upon a Triaryl-substituted Pharmacophore. 241$^{st}$ American Chemical Society National Meeting. Anaheim, California. USA. Mar. 27-31, 2011.*

* cited by examiner

*Primary Examiner* — Samantha Shterengarts

(57) ABSTRACT

This invention offers an effective method of inhibiting the expression of apolipoprotein E by mammalian cells. Apolipoprotein E is a protein that plays a significant role in the development of Alzheimer's Disease in humans. The method comprises administering an effective amount of a triarylmethyl amine compound having the general formula:

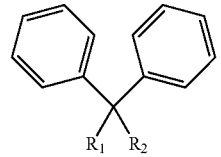

wherein the $R_1$ group may comprise acyclic amines and aliphatic amines. The $R_2$ group may comprise one of three aryl varieties: aryl, substituted aryl, or heterocycle. Triarylamine compounds inhibit apolipoprotein E expression in mammalian cells. In one aspect of the invention the mammalian cells may be human cells, and more specifically may be human brain cells.

8 Claims, 2 Drawing Sheets

METHOD OF INHIBITING APOLIPOPROTEIN-E EXPRESSION COMPRISING ADMINISTERING A TRIARYLMETHYL AMINE COMPOUND

RELATED APPLICATIONS

This is a divisional application of Ser. No. 13/536,738 filed on Jun. 28, 2012, and currently pending.

BACKGROUND OF THE INVENTION

Alzheimer's Disease is a common form of dementia associated with memory loss, intellectual function decline, depression, and disorientation. Alzheimer's Disease affects more than 5 million people in the United States and costs over $200 billion every year. (Alzheimer's Association, *The Journal of the Alzheimer's Association* (2012) 8: 131-168.) It is found in 13% of the population over the age of 65 and 45% of the population over the age of 85. (Alzheimer's Association, *The Journal of the Alzheimer's Association* (2012) 8: 131-168.) With a rapidly aging American population, prevalence of Alzheimer's Disease is expected to increase 2.5-fold to 13 million people in the United States in the next few decades. (Hebert et al., *Arch Neurol* (2003) 60: 1119-1122). Alzheimer's Disease will continue to be a major and expensive health crisis.

Alzheimer's Disease is typified by increased deposition of amyloid beta plaques and neurofibrillary tangles in the brain. More than 95% of the cases are considered "sporadic" and affect individual older than 65 years of age (late-onset). These cases are distinguished from the rare, early-onset, genetically-linked cases where production and deposition of amyloid beta plaques is higher. (Bateman et al., *Alzheimer's Res Ther*. (2011) 3: 1-13). Individuals with late-onset Alzheimer's Disease produce amyloid beta plaques at a normal rate and level, but have a reduced ability to clear the amyloid beta plaques from the brain. (Mawuenyega, et al., *Science* (2010) 330: 1774.)

Apolipoprotein-E (apoE) is a cholesterol- and lipid-carrier that has been implicated in aging, atherosclerosis and several neurological diseases including Alzheimer Disease. (Mahley, et al., *J Clin Invest* (2006) 116: 1226-9, Thorngate, et al., *Vasc Biol* (2000) 20: 1939-45, Fullerton, et al., *Exp Neurol* (2001) 169: 13-22, Ji, et al., *Neuroscience* (2003) 122: 305-15, and Dergunov, et al., *Biochemistry (Mosc)* (2006) 71: 707-12.) ApoE genotype is the biggest risk factor for Alzheimer's Disease and may account for 60-90% of the genetic variance associated with Alzheimer's Disease. (Raber, et al., *Neurobiol Aging* (2004) 25: 641-50.)

There are three common isoforms (alleles) of apoE in humans: apoE2, apoE3, and apoE4—which contribute to the pleiotropic effects observed in human cognition and neurodegenerative diseases. (Bales, et al., *Proc Natl Acad Sci USA* (1999) 96: 15233-3, Holtzman, et al., *J Clin Invest* (1999) 103: 15-21.) Several lines of evidence support the idea that the human apoE4 is hypofunctional and is considered to be the "bad" apoE, while apoE3 is the most common isoform and is considered to be the "normal" apoE. (Mahley, et al., *Proc Natl Acad Sci USA* (2006) 95:7585-90, and Hauser, et al., *Prog Lipid Res* (2011) 50: 62-74.) The risk for Alzheimer's Disease is two- and seven-fold higher in subjects that are heterozygous and homozygous, respectively, for apoE4. (Corder, et al., *Science* (1993) 261:921-3.) The age of disease onset is also accelerated by 6-8 years for each inherited copy of apoE4. (Corder, et al., *Science* (1993) 261:921-3.) Several groups consider the apoE4 allele to be detrimental because the apoE4 protein aggregate with amyloid beta plaques more readily than the apoE3 protein and apoE4 is less effective at clearing the amyloid beta plaques from the brain (Tokuda, et al., *Biochem J* (2000) 348: 359-65, Castellano, et al., *Sci Transl Med* (2011) 3:895-7, and Buttini, et al., *Neuroscience* (2000) 97:207-10.). These and other neurodegenerative effects have led some to conclude that apoE4 protein behaves like a "dominant-negative mutant," is "a causative factor" in Alzheimer's Disease pathogenesis, and a "neglected opportunity" for treatment of Alzheimer's Disease. Thus, there is a strong interest in the biomedical community to find therapies that can reduce apoE levels. These therapies are of value to all individuals, and especially to subjects that have apoE4 allele(s).

Unlike humans, most other mammals have only one common apoE allele (Mahley and Rall, *Annu Rev Genomics Hum Genet* (2000) 1:507-37.) Increase in levels of murine apoE in a mouse model of Alzheimer's Disease by Bexarotene, an FDA-approved cancer drug, has been considered to be of therapeutic relevance because of the associated clearance of soluble amyloid beta as well as amyloid beta plaques. (Cramer, et al., *Science* (2012) 335: 1503-6.) However, more than half of the subjects suffering from Alzheimer's Disease have at least one copy of the "bad" apoE4 allele, and thus there is the need for inhibiting apoE gene expression in these individuals. (Raber, et al., *Neurobiol Aging* (2004) 25: 641-50, Corder, et al., *Science* (1993) 261:921-3.)

Since the American population is aging, and the percentage of American people with Alzheimer's Disease is expected to increase, there is the need to further develop small organic molecules that can be easily administered to slow or stop the progression of the disease. Since apoE4 protein is detrimental to clearing amyloid beta plaques from brain tissue, any developed organic molecule that can be administered to people to stop the expression of apoE4 would likely have implications in Alzheimer's Disease treatments.

SUMMARY OF THE INVENTION

The present invention is directed to a method of inhibiting the expression of apolipoprotein E (apoE) by mammalian cells comprising administering an effective amount of a triarylmethyl amine compound having general formula (I):

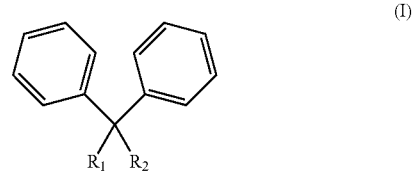

(I)

wherein $R_1$ group comprises the general formula (II):

(II)

wherein each of $R_3$ and $R_4$ independently is hydrogen, alkyl, substituted alkyl, aryl, substituted aryl, or heterocycle, and $R_2$ is aryl, substituted aryl, or heterocycle.

In one aspect of the invention, the $R_1$ group having general formula (II) may be a member selected from the group consisting of:

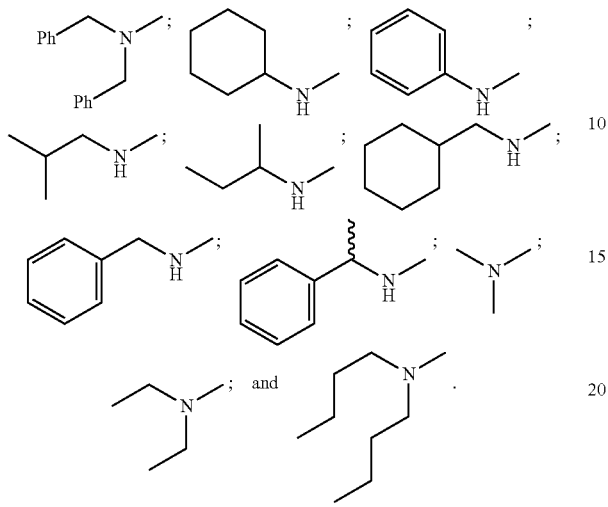

In another aspect of the invention, the general formula (I) comprises an $R_1$ group that comprises the general formula (III):

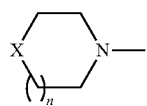

(III)

and X is alkyl, N, or S, and n is 0 or 1. The $R_1$ group having general formula (III): may be a member selected from the group consisting of:

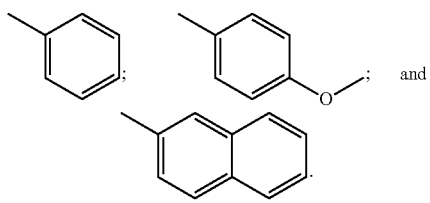

In a third aspect of the invention, the $R_2$ group for triarylmethyl amine compounds having either an $R_1$ group comprising general formula (II) or general formula (III) may be a member selected from the group consisting of:

In further aspects of the invention, the mammalian cells may be human cells, and may be human brain cells.

In preferred embodiments of the invention, a triarylmethyl amine compound has general formula (I) with an $R_1$ group having general formula (II) wherein the $R_1$ is

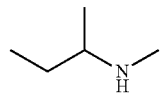

and the $R_2$ is

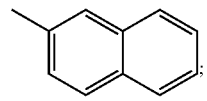

or wherein the $R_1$ is

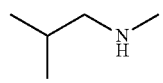

and the $R_2$ is

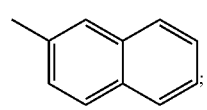

or wherein the $R_1$ is

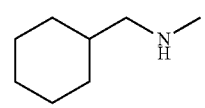

and the $R_2$ is

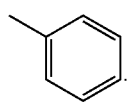

In another preferred embodiment, a triarylmethyl amine compound has general formula (I) with an $R_1$ group having general formula (III) wherein the $R_1$ is

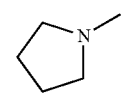

and the $R_2$ is

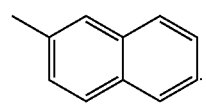

DETAILED DESCRIPTION OF THE INVENTION AND PREFERRED EMBODIMENTS

Figure 1:
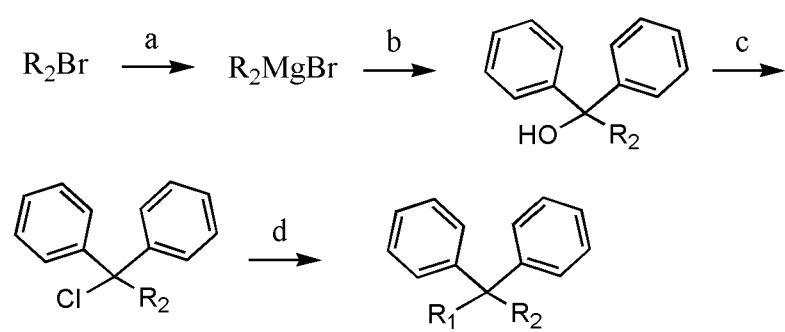
FIG. 1 shows the process for synthesizing triarylmethyl amine compounds.

The present invention relates to triarylmethyl amine compounds and methods for inhibiting the expression of apolipoprotein E (apoE) by mammalian cells.

The present invention relates to a number of small-molecule compounds which are capable of inhibiting the expression levels of apoE by mammalian cells when the compounds are administered in effective amounts. These small-molecule compounds are structurally described as triarylmethyl amines and have the general structure (I):

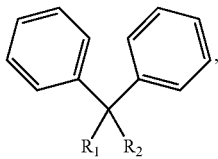

(I)

wherein $R_1$ may have two general structures, general structure (II):

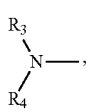

(II)

and general structure (III):

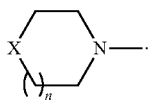

(III)

For general structure (III), the X may be alkyl, N, or S, and n may be 0 or 1.

A. Definitions

The term "inhibiting" as used herein is used interchangeably with the following: reducing, slowing, stopping, obstructing, impeding, and preventing.

The term "expression" as used herein defines the process of gene expression including one, some or all of the following steps: transcription, RNA splicing, RNA stabilization, translation, and post-translational modification.

The term "administering" as used herein may be used interchangeably with the following: contacted with, passed over, incubated with, combined with, flowed over, and added to.

The term "effective amount" as used herein defines an amount of a given triarylmethyl amine compound administered to mammalian cells which results in an objectively quantifiable reduction in apoE protein production in at least some of those cells as observed or noted by a scientist, clinician, or other qualified observer of ordinary skill in the art.

The term "independently" as used herein indicates that the $R_3$ and $R_4$ groups of general formula (II) can be identical or different. The $R_3$ and $R_4$ groups may both be phenyl, or the $R_3$ group may be phenyl and the $R_4$ group may be hydrogen.

B. Triarylmethyl Amine Compounds

Triarylmethyl amines are compounds having a tetravalent carbon bonded to two phenyl groups, an amine-containing member characterized by $R_1$, and a cyclic member characterized by $R_2$. There are two general versions of the $R_1$ member: general formula (II):

(II)

and general formula (III):

(III)

For general formula (II), the $R_3$ and $R_4$ groups may independently be hydrogen, alkyl, substituted alkyl, aryl, substituted aryl, or heterocycle. For general formula (III), the X may be a carbon, a nitrogen, an oxygen, or a sulfur, while the n may be 0 or 1. The triarylmethyl amine compounds as disclosed have molecular weights ranging from about 288 kDa to about 490 kDa.

Triarylmethyl amines were identified as candidates for inhibiting apoE expression in an initial pilot screening. The initial apoE screening was performed on a small library of compounds. Our goal was to screen a collection of hydrocarbon-rich small organic molecules based upon simple scaffolds that could be easily synthesized. Three scaffolds, viz., benzophenone ($R_1$—CO—$R_2$, where $R_1$ and $R_2$ are aryl groups), benzoin ($R_1$—CO—COR$_2$—$R_3$, where $R_1$ and $R_3$ are aryl groups and $R_2$ is benzyl group), and triarylmethyl amine ($R_1$—C(Ph)$_2$-$R_2$, where $R_1$ is a secondary or, tertiary amine and $R_2$ is an aryl group) were selected.

Altogether, two benzophenones, three benzoins, and 37 triarylmethyl amines were designed, synthesized, and screened, leading to the identification of the triarylmethyl amine scaffold ($R_1$—C(Ph)$_2$-$R_2$), represented herein as general formula (I), having the desired biological activity of inhibiting apoE expression. The pilot screen consisted of a total of nine compounds that included the two benzophenones, three benzoins and four triarylmethyl amines. The triarylmethyl amine scaffold provided the needed pharmacophore for apoE inhibition whereas the two other scaffolds proved inactive. These results led to the expansion of the triarylmethyl amine scaffold series to another set of 34 compounds. The diversity was introduced at the $R_1$ group with 15 amines that comprised alkyl and aryl groups including cyclic structures. The $R_2$ group was further extended to a substituted phenyl and naphthyl ring.

After the initial screening step, the 37 triarylmethyl amine compounds were subjected to a quantitative structure-activity-relationship (SAR) approach, which is well-known in the art. The SAR analysis of the 37 triarylmethyl amines showed that a naphthalene ring served most effectively as an $R_2$ group and that five specific amine groups served most effectively as an $R_1$ group for greatest inhibitory effect: morpholine, pyrrolidine, isobutylamine, sec-butylamine, and cyclohexylmethyl amine. Those 37 triarylmethyl amine compounds are listed in Table 1. Attention was paid to include hydrogen bonding donor and acceptor amines in the final compounds, to vary the size of the third aromatic ring and also to include acyclic and cyclic amines of varying sizes and shapes.

TABLE 1

Triarylmethyl Amine Compounds Comprising Combinations of Three R₂ Group Aryl Variants and Fifteen R₁ Group Amine Variants.

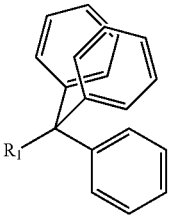

| Compound No | R1 |
|---|---|
| 1 |  |
| 2 |  |
| 3 | 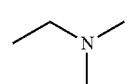 |
| 4 | 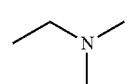 |
| 5 |  |
| 6 | 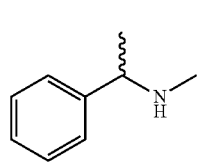 |
| 7 | 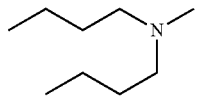 |
| 8 | 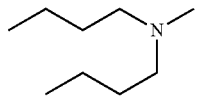 |
| 9 | 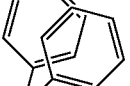 |
| 10 | 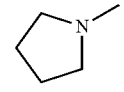 |

TABLE 1-continued

Triarylmethyl Amine Compounds Comprising Combinations of Three R₂ Group Aryl Variants and Fifteen R₁ Group Amine Variants.

| Compound No | R1 |
|---|---|
| 11 | 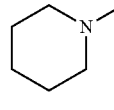 |
| 12 | 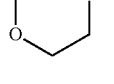 |
| 13 | 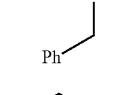 |
| 14 | 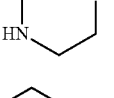 |
| 15 | 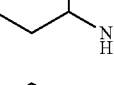 |

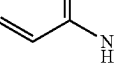

| Compound No | R1 |
|---|---|
| 16 | 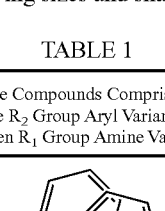 |
| 17 |  |
| 18 | 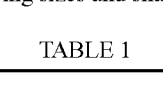 |
| 19 | 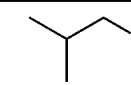 |
| 20 |  |
| 21 | 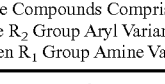 |

TABLE 1-continued

Triarylmethyl Amine Compounds Comprising Combinations of Three $R_2$ Group Aryl Variants and Fifteen $R_1$ Group Amine Variants.

| | |
|---|---|
| 22 | 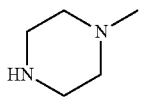 |
| 23 | 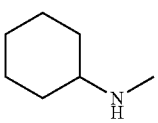 |
| 24 | 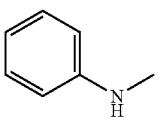 |
| 25 | 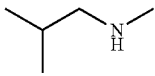 |
| 26 | 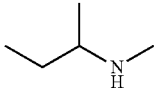 |
| 27 | 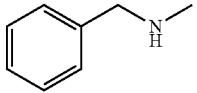 |

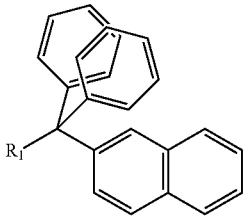

| Compound No | R1 |
|---|---|
| 28 |  |
| 29 | 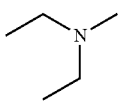 |
| 30 | 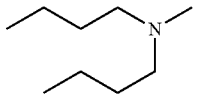 |
| 31 | 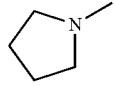 |
| 32 | 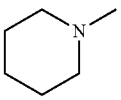 |

TABLE 1-continued

Triarylmethyl Amine Compounds Comprising Combinations of Three $R_2$ Group Aryl Variants and Fifteen $R_1$ Group Amine Variants.

| | |
|---|---|
| 33 | 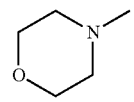 |
| 34 | 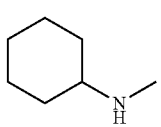 |
| 35 | 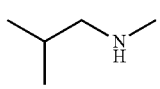 |
| 36 | 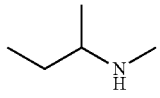 |
| 37 | 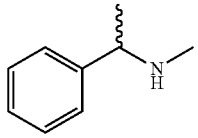 |

Table 1 shows an illustrative sample of synthesized triarylmethyl amine compounds. Each triarylmethyl amine compound disclosed in Table 1 has two phenyl rings, a third aryl ring and a unique amine member. Para-methoxyphenyl and naphthyl aromatic groups were selected, along with a plain phenyl group, as the $R_2$ group for several compounds in order to test the effect of varying size without altering polarity in this area of the molecule.

Altogether, fifteen different primary and secondary amines provide added diversity for the triarylmethyl amine molecules. As shown in Table 1, the $R_1$ amines include aliphatic acyclic amines, such as dimethyl amine, diethyl amine, and dibutyl amine. The $R_1$ amines also include aliphatic, cyclic amines, such as pyrrolidine, piperidine and morpholine. Secondary amines include cyclohexyl amine, aniline, isobutyl amine, and sec-butyl amine. A racemic version of α-methylbenzyl amine group is the only chiral example of amine in the secondary amine category. Activity arising from a molecule comprising α-methylbenzyl could reveal fine details regarding the molecular level interaction of the agent in the biological system. The initial nature of the selected amine dictated the hydrogen bonding capability of the final compounds shown in Table 1. Some of these compounds, e.g., Compounds 7, 20 and 33 have hydrogen-bond acceptor regions as tertiary amines, whereas others, e.g., Compounds 15, 22, 35 and 36 have hydrogen-bond acceptor regions as secondary amines.

As shown in FIG. 1, the synthesis of triarylmethyl amine compounds starts with creating an aromatic bromide including the $R_2$ group. Then the aromatic bromide structure is converted through step (a) into a Grignard reagent. Step (a) includes subjecting the aromatic bromide to magnesium metal using diethyl ether as the solvent under refluxing anhydrous conditions for 3 hours. The result of step (a) is the formation of a phenyl magnesium bromide incorporating the $R_2$ group. Next, in step (b), the magnesium bromide compound is subjected to benzophenone to create the tertiary alcohol, triphenylmethanol, incorporating the $R_2$ group and the reaction was allowed to continue in refluxing ether medium for 15 hours. Step (c) comprises subjecting the triphenylmethanol compound incorporating the $R_2$ group to acetyl chloride and a refluxing benzene solvent for 3 hours to create the triphenylmethyl chloride compound incorporating the $R_2$ group.

Step (d) comprises $S_N1$ substitution reactions involving subjecting the triphenylmethyl chloride compound to an amine compound with the $R_1$ group, triethylamine, and methylene chloride. These $S_N1$ substitution reactions were carried out in an aprotic polar solvent, such as methylene chloride, in single and parallel reaction set ups with one or more $R_1$ amines in slight stoichiometric excess. Aqueous wash, followed by mild acid wash removed some of the unreacted, excess amine. Both primary and secondary amines were selected with varying length of alkyl chains and aryl groups. Acyclic and cyclic moieties were chosen and some of the amines contained additional heteroatoms. In step (d) the triarylmethyl chloride intermediate is converted into the final triarylmethyl amine product by substituting with an amine nucleophile.

The synthesis procedure shown in FIG. 1 results in the formation of triarylmethyl amine compounds having the general formula

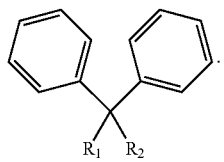

For the inventions described herein, the $R_2$ group comprised a member selected from the group consisting of:

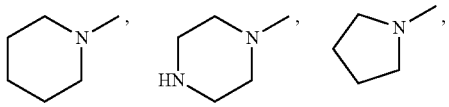

Successful purification of these resulting triarylmethyl amine compounds was effected by pre-soaking silica gel with an eluent, e.g. ethyl acetate:hexane mixture, containing small amounts of triethylamine while performing standard flash columns, preparatory thin layer chromatography or radial chromatography.

The $R_1$ amine group was created by displacing the chloro-functionality generated from the triarylmethyl alcohol with various primary and secondary amines. The synthesized chloro-intermediate was split into several reactions with the chosen amines. The subsequent $S_N1$ reaction introduced the amine group and created the final product structure. The incoming primary amine led to the formation of a secondary amine product and a secondary amine formed a tertiary amine at the end. These two classes differed in their hydrogen-bonding capabilities, the former being a hydrogen bond donor and the latter being hydrogen bond acceptor.

The overall yield for the triarylmethyl amine compound synthesis is between about 39% and about 85%. The factors that affect the percentage yield are the intrinsic nature of the amines, their 3-dimensional size, and shape.

The synthesis procedure shown in FIG. 1 can be carried out manually by a laboratory technician or it can be automated by applying parallel chemistry techniques at the end of the synthetic scheme. So, the amination reaction of the triarylmethyl chloride can be performed with various amines not only in parallel, but also by applying combinatorial chemistry techniques for significantly faster turnaround.

The triarylmethyl amine compounds with the para-methoxyphenyl $R_2$ group were less stable than the triarylmethyl amine compounds with either the phenyl aromatic $R_2$ group or the naphthalene aromatic $R_2$ group used for the triarylmethyl amine scaffold. The instability may be attributed to the ease of triarylmethyl carbocation formation due to the presence of a strong electron-donating methoxy group.

One of ordinary skill in the art, based on the synthesis description herein, can formulate the described triarylmethyl amine compounds using conventional synthetic chemistry techniques. The following specific examples, which describe the synthesis of several compounds of this invention, are to be construed as merely illustrative and not limiting of the disclosure in any way.

EXAMPLE 1

Synthesis of Triarylmethyl amine
4-(Naphthalen-2-yl-diphenyl-methyl)-morpholine
(Shown as Compound 33 in Table 1)

Scratched magnesium turnings (1.056 g, 43.4 mmol) were placed in a 250 mL round-bottomed, 3-neck flask at room temperature. A small portion of the solution of 2-bromonaphthalene (11.84 g, 47.7 mmol) in anhydrous ether (40 mL) was added through an addition funnel and the solution was heated to gentle reflux maintaining the temperature at 35° C. The rest of the solution was added in small fractions over a period of 1 hour, and the resulting reaction mixture was refluxed for an additional 1 hour. Disappearance of all magnesium indicated the completion of the reaction.

The solution containing benzophenone (7.04 g, 38.6 mmol) in anhydrous ether (20 mL) was added through an additional funnel all at once over 2-4 minutes. The resulting reaction was gently refluxed for 24 hours. The cooled mixture was slowly and carefully quenched by adding aqueous HCl (6M) to the reaction mixture until the pH was acidic as tested by litmus paper. The mixture was diluted with ether (30 mL) and the aqueous layer was removed. The ether layer was washed with water (30 mL), followed by brine (30 mL) and dried with anhydrous $Na_2SO_4$. After filtration, the solvent was removed under reduced pressure to provide a colorless solid (triarylmethyl alcohol).

The crude triaryl alcohol derivative (6.30 g, 20.3 mmol) was refluxed with acetyl chloride (2.2 mL, 30.45 mmol) in benzene (10 mL) for 5 min. An additional amount of acetyl chloride (2.5 mL) was added over the course of 10 min. via an addition funnel, and the resulting solution was allowed to reflux for another 30 min. The solution was quickly cooled by holding the flask under a stream of running water while vigorously shaking the mixture. The mixture was concentrated under reduced pressure to give the triaryl chloride derivative.

The crude triarylmethyl chloride derivative and morpholine (5.0 mL, 57.9 mmol) in anhydrous $CH_2Cl_2$ (25 mL) was stirred at 25° C. for 18 hours. The organic layer was washed with water (30 mL) followed by saturated $NaHCO_3$ solution (30 mL) and brine (30 mL), and then dried with anhydrous $Na_2SO_4$. The solution was filtered and the solvent was evaporated under reduced pressure to yield crude triarylmethyl amine 4-(naphthalen-2-yl-diphenyl-methyl)-morpholine as a dirty white solid. Flash chromatography using 230-400 mesh silica gel was performed to purify compound 33. Elution of the column with 30% ethyl acetate in hexanes, followed by concentration of the appropriate fractions and subsequent evaporation of solvents yielded 6.88 g (47% overall yield) of triarylmethyl amine 4-(naphthalen-2-yl-diphenyl-methyl)-morpholine as an off-white amorphous solid.

EXAMPLE 2

Synthesis of Triarylmethyl amine:
Diethyl-[(4-methoxy-phenyl)-diphenyl-methyl]-amine
(Shown as Compound 17 in Table 1)

The reaction was carried out on a $\frac{1}{10}^{th}$ scale compared to EXAMPLE 1, starting with scratched magnesium turnings (0.110 g, 4.3 mmol) placed in a 250 mL round-bottomed, 3-neck flask at room temperature. A small portion of the solution of 2-bromonaphthalene (1.18 g, 47.7 mmol) in anhydrous ether (4 mL) was added through an addition funnel and the solution was heated to gentle reflux maintaining the temperature at 35° C. The rest of the solution was added in small fractions over a period of 1 hour, and the resulting reaction mixture was refluxed for an additional 1 hour. Disappearance of all magnesium indicated the completion of the reaction.

The solution containing benzophenone (0.7 g, 38.6 mmol) in anhydrous ether (2 mL) was added through an additional funnel over 2-4 minutes. The resulting reaction was gently refluxed for 24 hours. The cooled mixture was slowly and carefully quenched by adding aqueous HCl (6M) to the reaction mixture until the pH was acidic as tested by litmus paper. The mixture was diluted with ether (3 mL) and the aqueous layer was removed. The ether layer was washed with water (3 mL), followed by brine (3 mL) and dried with anhydrous $Na_2SO_4$. After filtration, the solvent was removed under reduced pressure to provide a colorless solid (triarylmethyl alcohol).

The crude triarylmethyl alcohol derivative (0.6 g, 20.3 mmol) was refluxed with acetyl chloride (0.2 mL, 30.45 mmol) in benzene (1 mL) for 5 min. An additional amount of acetyl chloride (0.3 mL) was added over the course of 10 min. via an addition funnel, and the resulting solution was allowed to reflux for another 30 min. The solution was quickly cooled by holding the flask under a stream of running water while vigorously shaking the mixture. The mixture was concentrated under reduced pressure to give the triarylmethyl chloride derivative.

The crude triarylmethyl chloride was then reacted with diethyl amine (0.63 mL, 6.1 mmol) in anhydrous $CH_2Cl_2$ (3 mL) and stirred at 25° C. for 18 hours. The organic layer was washed with water (3 mL) followed by saturated $NaHCO_3$ solution (3 mL) and brine (3 mL), and then dried with anhydrous $Na_2SO_4$. The solution was filtered and the solvent was evaporated under reduced pressure to yield crude diethyl-[(4-methoxy-phenyl)-diphenyl-methyl]-amine as a thick colorless liquid.

Flash chromatography using 230-400 mesh silica gel was performed to purify diethyl-[(4-methoxy-phenyl)-diphenyl-methyl]-amine. Elution of the column with 20% ethyl acetate and 3% triethylamine in hexanes, followed by concentration of the appropriate fractions and subsequent evaporation of solvents yielded 0.487 g (33% overall yield) of diethyl-[(4-methoxy-phenyl)-diphenyl-methyl]-amine as an off-white semi-solid material.

C. Biological Effect Of The Triarylmethyl Amine Compounds

The compounds of this invention have been found to be potent inhibitors of apoE expression. As such, this invention contemplates using the compounds of this invention to inhibit apoE expression in mammalian cells, either in vivo or in vitro. The compounds of this invention may inhibit apoE expression specifically in human cells, and more specifically in human brain cells. In one embodiment, the present invention provides a method of inhibiting apoE expression by administering an effective amount of the described triarylmethyl amine compounds of this present invention to human cells. In another embodiment, the present invention provides a method of inhibiting apoE expression by administering an effective amount of the described triarylmethyl amine compounds to human brain cells.

ApoE inhibition can be readily determined by any one of several assays and techniques known to those of ordinary skill in the art, including the enzyme-linked immunosorbent assay (ELISA) and quantitative reverse transcription-polymerase chain reaction (qPCR). The assays were used to analyze apoE expression in CCF-STTG1 astrocytoma cells, H4 neuroglioma cells, and HepG2 human hepatocellular carcinoma cells.

CCF-STTG1 is a human astrocytoma cell line. Astrocytes are the primary producers of apoE in the brain and expression of apoE in astrocytes increases with age, as well as progression of Alzheimer's Disease and/or brain injury. (Bien-Ly, et al., *J Neurosci* (2012) 32:4803-11.) ApoE expression in CCF-STTG1 cells is robust and is responsive to known activators of apoE regulation (Krul and Tang, *J Neurosci Res* (1992) 32:227-38; Liang, et al., *J Neurochem* (2004) 88:623-34; Abildayeva, et al., *J Biol Chem* (2006) 281:12799-808.).

H4 human neuroglioma cell line is a widely-used model system for Alzheimer's Disease research (Samy and Igwe, *J Mol Neurosci* (2012) 47:533-45; Kukar, et al., *Nature* (2008) 453:925-9; Kinoshita, et al., *J Biol Chem* (2002) 277:28530-6.). Levels of secreted apoE protein are low in this cell type but steady-state apoE mRNA levels are easily detectable by quantitative PCR for apoE in the H4 cDNA.

HepG2 human hepatocellular carcinoma line is a commonly used hepatocyte model system. This cell line has a lipoprotein secretion profile that matches with in vivo data, and expresses apoE at detectable levels. (Dashti, et al., *J Lipid Res* (1987) 28:423-36.)

i. ELISA Data Show Triarylmethyl Amine Compounds Inhibit ApoE Expression.

The triarylmethyl amine compounds, including the ones shown in TABLE 1, were tested for biological effects on mammalian cells in an ELISA, an assay well-known in the art. Specifically, the triarylmethyl amine compounds were tested for biological effects on human CCF-STTG1 astrocytoma cells which are a model cell line for astrocytes found in the brain. The ELISA technique involves immobilizing an apoE-specific capture antibody to a 96-well plate, addition of sample (conditioned medium from astrocytoma cells treated with the compound for 24 hours), and detection of the bound apoE using a second apoE-specific biotinylated antibody and streptavidin-HRP.

The ELISA's used in this invention were obtained from Mabtech, Inc. which sells the relevant ELISA as Human apoE ELISA kit (item code 3712-1H-20). The Mabtech ELISA kit detects the presence of three apoE isoforms: apoE2, apoE3, and apoE4.

EXAMPLE NO. 3

Figure 2:
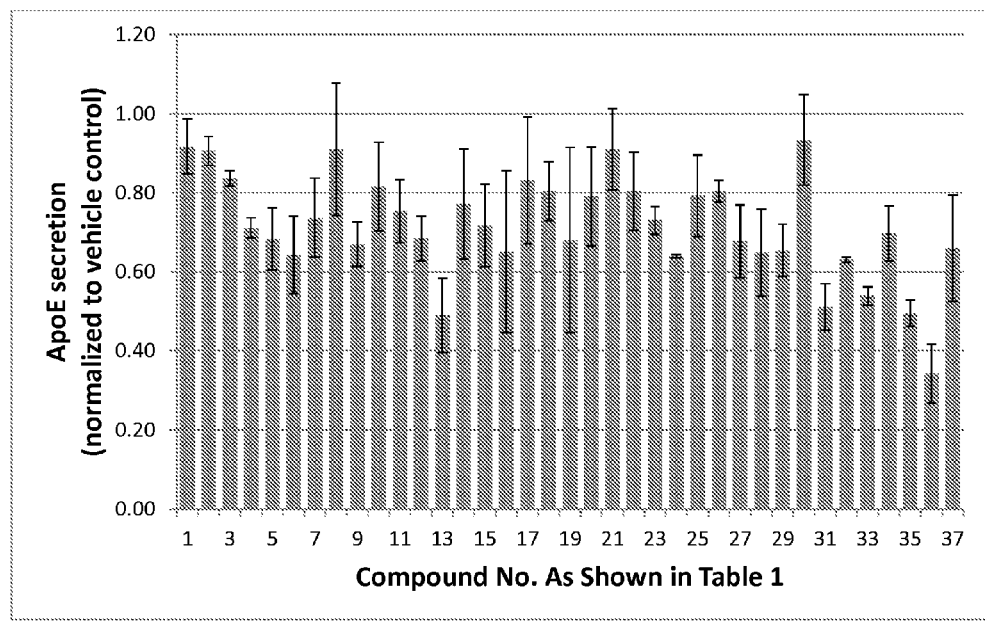
FIG. 2 is a chart that shows the inhibitory effect of triarylmethyl amine compounds on apoE expression as analyzed by ELISA in human CCF-STTG1 astrocytoma cells.

Triarylmethyl Amine Compounds Administered to Human CCF-STTG1 Astrocytoma Cells and Analyzed by ELISA To obtain the data shown in Table 2, Table 3, and FIG. 2, the human CCF-STTG1 astrocytoma cells (ATCC, CRL-1718)

were maintained in RPMI medium (Mediatech) supplemented with 10 mM HEPES, 1 mM sodium pyruvate, 4.5 g/L glucose, 1% penicillin/streptomycin, and 10% bovine growth serum (HyClone) at 37° C. with 5% $CO_2$ All triarylmethyl amine compounds listed in Table 1 were individually dissolved in DMSO at a stock concentration of 10 mM and individually tested. For ELISA's, $1.6 \times 10^4$ cells/96-well were grown for 1 day in RPMI, followed by a 24 hour equilibration in serum-free Opti-MEM (Life Technologies). Treatments were carried out in quadruplicate with 100 μL of fresh Opti-MEM containing 10 μM of compound or vehicle (0.1% DMSO) for 24 hours. Conditioned medium from these samples were then diluted 2-fold with incubation buffer (PBS+0.05% Tween-20+0.1% BSA) and analyzed with a human apoE HRP ELISA kit (Mabtech) according to the manufacturer's protocol. ApoE concentration in the sample was calculated based on a standard curve derived using known amounts of purified apoE supplied with the kit. The cells in the 96-well plates were used to determine the total cell number using CyQUANT reagent (Life Technologies). Sample apoE concentrations were adjusted for total cell number and then normalized to DMSO treated cells, which provides an effective control for the experimental triarylmethyl amine compounds. Results for each set of compounds tested in parallel (n=3) were analyzed by a one-tailed t-test.

Table 2 and FIG. 2 show the ELISA data quantifying the biological effects of individual triarylmethyl amine compounds on human astrocytoma cells (CCF-STTG1 cell line). The astrocytoma cells were treated for 24 hours with a 10 μM concentration of each of the individual 37 compounds listed in Table 1.

As shown in Table 2 and FIG. 2, triarylmethyl amine compounds are very effective at inhibiting the expression of apoE in human astrocytoma cells.

TABLE 2

Inhibitory Effect of Triarylmethyl Amine Compounds on Human CCF-STTG1 Astrocytoma Cell ApoE Production as Determined by ELISA.

| Triarylmethyl Amine Compound No. (as listed in Table 1) | ApoE (ng/ml) Normalized for Cell Count and Vehicle Treatment | Standard Deviation in Structural Equation Modeling (S/T SEM) | Inhibition Percentage of ApoE Expression |
|---|---|---|---|
| 1 | 0.92 | 0.07 | 8 |
| 2 | 0.91 | 0.04 | 9 |
| 3 | 0.84 | 0.02 | 16 |
| 4 | 0.71 | 0.03 | 29 |
| 5 | 0.68 | 0.08 | 32 |
| 6 | 0.64 | 0.10 | 36 |
| 7 | 0.74 | 0.10 | 26 |
| 8 | 0.91 | 0.17 | 9 |
| 9 | 0.67 | 0.06 | 33 |
| 10 | 0.82 | 0.11 | 18 |
| 11 | 0.75 | 0.08 | 25 |
| 12 | 0.68 | 0.06 | 32 |
| 13 | 0.49 | 0.09 | 51 |
| 14 | 0.77 | 0.14 | 23 |
| 15 | 0.72 | 0.10 | 28 |
| 16 | 0.65 | 0.21 | 35 |
| 17 | 0.83 | 0.16 | 17 |
| 18 | 0.80 | 0.07 | 20 |
| 19 | 0.68 | 0.23 | 32 |
| 20 | 0.79 | 0.13 | 21 |
| 21 | 0.91 | 0.10 | 9 |
| 22 | 0.80 | 0.10 | 20 |
| 23 | 0.73 | 0.04 | 27 |
| 24 | 0.64 | 0.00 | 36 |
| 25 | 0.79 | 0.10 | 21 |
| 26 | 0.80 | 0.03 | 20 |
| 27 | 0.68 | 0.09 | 32 |
| 28 | 0.65 | 0.11 | 35 |
| 29 | 0.65 | 0.07 | 35 |
| 30 | 0.93 | 0.11 | 7 |
| 31 | 0.51 | 0.06 | 49 |
| 32 | 0.63 | 0.01 | 37 |
| 33 | 0.54 | 0.02 | 46 |
| 34 | 0.70 | 0.07 | 30 |
| 35 | 0.50 | 0.03 | 50 |
| 36 | 0.34 | 0.07 | 66 |
| 37 | 0.66 | 0.13 | 34 |

The expanded synthesis of the triaryalmethyl amine compound series yielded much greater apoE inhibitory activity than shown in the initial screen. Both the para-methoxyphenyl and the naphthalene groups showed better apoE inhibition than the originally synthesized phenyl series, with the naphthalene group resulting in strong inhibition of apoE production.

As shown in Table 2, cyclohexylmethyl-trityl-amine, shown as Compound 13 in Table 1, with the $R_1$ group being cyclohexylmethyl amine and the $R_2$ group being phenyl exhibited about 51% apoE inhibition. The other very potent molecules had a naphthyl group in place of the $R_2$ group and the $R_1$ group being pyrrolidine (1-(naphthalen-2-yl-diphenyl-methyl)-pyrrolidine, compound 31; about 49% inhibition), morpholine (4-(naphthalen-2-yl-diphenyl-methyl)-morpholine, compound 33; about 46% apoE inhibition), isobutylamine (isobutyl-(naphthalen-2-yl-diphenyl-methyl)-amine, compound 35; about 50% inhibition), and sec-butylamine (sec-butyl-(naphthalen-2-yl-diphenyl-methyl)-amine, compound 36; about 66% inhibition).

The presence of hydrogen bond donor vs. acceptor groups at the amine functionality, or the acyclic vs. cyclic nature of the amine did not cause any noticeable change in the inhibitory activity. Six of the compounds (Table 1, Compound Nos. 28-33) have hydrogen bond donor groups and some (Table 1, Compound Nos. 34-37) have hydrogen bond acceptor groups and there is an equal mix of acyclic and cyclic structures around the amine group. The overall size of the amine group may play a role in determining the inhibition efficacy since all four triarylmethyl amine structures showing high ability to inhibit apoE production contain small amines. Compound Nos. 13, 31, 35 and 36, as listed in Table 1, comprise approximately 5-6 atoms.

EXAMPLE 4

Triarylmethyl Amine Compounds Administered to Human HepG2 Liver Cells and Analyzed by ELISA The triarylmethyl amine compounds disclosed in this invention were also tested on human liver cells, specifically human HepG2 liver cells. HepG2 cells are a well-known cell line that is commonly used for in vitro testing for protein expression and drug efficacy.

To obtain the data shown in Table 4, the human HepG2 liver cells (ATCC, HB-8065 were maintained in RPMI medium (Mediatech) supplemented with 10 mM HEPES, 1 mM sodium pyruvate, 4.5 g/L glucose, 1% penicillin/streptomycin, and 10% bovine growth serum (HyClone) at 37° C. with 5% $CO_2$ Compound Nos. 13, 31, 33, 35 or 36—as listed in Table 1—were individually dissolved in DMSO at a stock concentration of 10 mM and individually tested. For ELISA's, 1.6× $10^4$ cells/96-well were grown for 1 day in RPMI, followed by a 24 hour equilibration in serum-free Opti-MEM (Life Technologies). Treatments were carried out in quadruplicate with 100 μL of fresh Opti-MEM containing 10 μM of compound or vehicle (0.1% DMSO) for 24 hours. Conditioned medium from these samples were then diluted 2-fold with incubation buffer (PBS+0.05% Tween-20+0.1% BSA) and analyzed with a human apoE HRP ELISA kit (Mabtech) according to the manufacturer's protocol.

A standard curve was used to derive sample apoE concentrations. The cells in the 96-well plates were used to determine the total cell number using CyQUANT reagent (Life Technologies). Sample apoE concentrations were adjusted for total cell number and then normalized to DMSO treated wells. Results for each set of compounds tested in parallel (n=3) were analyzed by a one-tailed t-test.

Table 3 shows the ELISA data quantifying the biological effects of individual triarylmethyl amine compounds on human HepG2 liver cells. The data in Table 3 were obtained by using an apoE ELISA assay to monitor human HepG2 cell production of apoE after the HepG2 cells were treated with Compound Nos. 13, 31, 33, 35 and 36, as listed on Table 1. The HepG2 liver cells were treated for 24 hours with a 10 μM concentration of each of Compound Nos. 13, 31, 33, 35 and 36, as listed on Table 1.

TABLE 3

Inhibitory Effect of Triarylmethyl Amine Compounds on Human HepG2 Liver Cell ApoE Production as Determined by ELISA.

| Triarylmethyl Amine Compound No. (as listed in Table 1) | ApoE (ng/ml) Normalized for Cell Count and Vehicle Treatment | Standard Deviation in Structural Equation Modeling (S/T SEM) |
|---|---|---|
| 13 | 1.03 | 0.09 |
| 31 | 0.64 | 0.16 |
| 33 | 0.77 | 0.08 |
| 35 | 0.78 | 0.03 |
| 36 | 0.81 | 0.06 |

While triarylmethyl amine compounds of this invention inhibit apoE production in human brain cells, the triarylmethyl amine compounds of this invention also inhibit human cells that are not brain cells. Specifically, triarylmethyl amine compounds of this invention also have an inhibitory effect on human liver cells.

ii. QPCR Data Show Triarylmethyl Amine Compounds Inhibit ApoE Expression.

Quantitative reverse transcription polymerase chain reaction (qPCR) is a laboratory technique used to amplify and quantify the steady-state levels of apoE messenger RNA (mRNA) by converting the copy DNA (cDNA). The targeted DNA molecule quantity can be determined as a relative amount when normalized to housekeeping genes. For qPCR, reverse transcription is used to quantify the amount of mRNA produced through the balance between transcription rate and degradation rates. The amount of mRNA available is the one factor which can affect the overall protein expression. Quantification of the cDNA produced during reverse transcription of the mRNA may be accomplished by detecting the fluorescent markers, such as fluorophores, that selectively hybridize with the DNA target.

EXAMPLE 5

Triarylmethyl Amine Compounds Administered to Human CCF-STTG1 Astrocytoma Cells and Analyzed by qPCR Analysis The CCF-STTG1 (ATCC, CRL-1718) human astrocytoma cells were treated with one of the selected triarylmethyl amine compounds for 24 hours in OptiMEM. The triarylmethyl amine compounds were selected from Compound Nos. 13, 31, 33, 35 and 36, as listed in Table 1. The selected triarylmethyl amine compounds were individually dissolved in DMSO at a stock concentration of 10 mM and individually tested. Total RNA was extracted using the RNeasy Plus Mini Kit (Qiagen). Genomic DNA (gDNA) was removed by centrifugation through gDNA eliminator spin columns included with the kit. Samples of total RNA were reverse transcribed following instructions in the Superscript III first strand synthesis kit (Life Technologies). ApoE, HPRT1, and β-actin cDNA levels were quantified by TaqMan multiplex quantitative PCR using a CFX96 Real-Time PCR Detection System (BioRad). Reactions were carried out with SensiMix II Probe Master Mix (Bioline) in a 20 μL total volume containing 5-30 ng of cDNA template. Fluorescent labels and primer/probe concentrations were as follows: apoE (5'-FAM, 600 nM/300 nM), HPRT1 (5'-TEX-615, 100 nM/25 nM), and β-actin (5'-Cy5, 100 nM/25 nM). ZEN double quenched probes (Integrated DNA technologies) were used for all apoE reactions. The reactions were performed in triplicate and the results were analyzed using qbasePLUS (Biogazelle) with HPRT1 and β-actin as housekeeping genes.

Table 4 shows the CCF-STTG1 astrocytoma cells under the influence of selected triarylmethyl amine compounds. Triarylmethyl amine compounds disclosed in this invention have an inhibitory effect on the mRNA produced by the CCF-STTG1 cells.

TABLE 4

Inhibitory Effect of Triarylmethyl Amine Compounds on CCF-STTG1 Astrocytoma Cell ApoE Production as Determined by qPCR Analysis.

| Triarylmethyl Amine Compound No. (as listed in Table 1) | ApoE (ng/ml) Normalized for Cell Count and Vehicle Treatment | Standard Deviation in Structural Equation Modeling (S/T SEM) |
|---|---|---|
| 13 | 1.10 | 0.07 |
| 31 | 0.86 | 0.06 |
| 33 | 0.88 | 0.01 |
| 35 | 0.87 | 0.05 |
| 36 | 0.85 | 0.03 |

EXAMPLE 6

Triarylmethyl Amine Compounds Administered to Human HepG2 Liver Cells and Analyzed by qPCR Analysis The HepG2 (ATCC, HB-8065) human liver cells were treated with one of the selected triarylmethyl amine compounds for 24 hours in OptiMEM. The triarylmethyl amine compounds were selected from Compound Nos. 13, 31, 33, 35 and 36, as listed in Table 1. The selected triarylmethyl amine compounds were individually dissolved in DMSO at a stock concentration of 10 mM and individually tested. Total RNA was extracted using the RNeasy Plus Mini Kit (Qiagen). Genomic DNA (gDNA) was removed by centrifugation through gDNA eliminator spin columns included with the kit. Samples of total RNA were reverse transcribed following instructions in the Superscript III first strand synthesis kit (Life Technologies). ApoE, HPRT1, and β-actin cDNA levels were quantified by TaqMan multiplex quantitative PCR using a CFX96 Real-Time PCR Detection System (BioRad). Reactions were carried out with SensiMix II Probe Master Mix (Bioline) in a 20 µL total volume containing 5-30 ng of cDNA template. Fluorescent labels and primer/probe concentrations were as follows: apoE (5'-FAM, 600 nM/300 nM), HPRT1 (5'-TEX-615, 100 nM/25 nM), and β-actin (5'-Cy5, 100 nM/25 nM). ZEN double quenched probes (Integrated DNA technologies) were used for all apoE reactions. The reactions were performed in triplicate and the results were analyzed using qbasePLUS (Biogazelle) with HPRT1 and β-actin as housekeeping genes.

Table 5 shows the HepG2 liver cells under the influence of selected triarylmethyl amine compounds. Triarylmethyl amine compounds disclosed in this invention have an inhibitory effect on the mRNA produced by the HepG2 liver cells.

TABLE 5

Inhibitory Effect of Triarylmethyl Amine Compounds on HepG2 Liver Cell ApoE Production as Determined by qPCR Analysis.

| Triarylmethyl Amine Compound No. (as listed in Table 1) | ApoE (ng/ml) Normalized for Cell Count and Vehicle Treatment | Standard Deviation in Structural Equation Modeling (S/T SEM) |
| --- | --- | --- |
| 13 | 1.16 | 0.07 |
| 31 | 0.86 | 0.24 |
| 33 | 1.22 | 0.11 |
| 35 | 1.03 | 0.22 |
| 36 | 0.93 | 0.06 |

EXAMPLE 7

Triarylmethyl Amine Compounds Administered to Human H4Neuroglioma Cells and Analyzed by qPCR Analysis The H4 human neuroglioma (ATCC, HTB-148) cells were treated with one of the selected triarylmethyl amine compounds for 24 hours in OptiMEM. The triarylmethyl amine compounds were selected from Compound Nos. 13, 31, 33, 35 and 36, as listed in Table 1. The selected triarylmethyl amine compounds were individually dissolved in DMSO at a stock concentration of 10 mM and individually tested. Total RNA was extracted using the RNeasy Plus Mini Kit (Qiagen). Genomic DNA (gDNA) was removed by centrifugation through gDNA eliminator spin columns included with the kit. Samples of total RNA were reverse transcribed following instructions in the Superscript III first strand synthesis kit (Life Technologies). ApoE, HPRT1, and β-actin cDNA levels were quantified by TaqMan multiplex quantitative PCR using a CFX96 Real-Time PCR Detection System (BioRad). Reactions were carried out with SensiMix II Probe Master Mix (Bioline) in a 20 µL total volume containing 5-30 ng of cDNA template. Fluorescent labels and primer/probe concentrations were as follows: apoE (5'-FAM, 600 nM/300 nM), HPRT1 (5'-TEX-615, 100 nM/25 nM), and β-actin (5'-Cy5, 100 nM/25 nM). ZEN double quenched probes (Integrated DNA technologies) were used for all apoE reactions. The reactions were performed in triplicate and the results were analyzed using qbasePLUS (Biogazelle) with HPRT1 and β-actin as housekeeping genes.

Table 6 shows the H4 neuroglioma cells under the influence of selected triarylmethyl amine compounds. Triarylmethyl amine compounds disclosed in this invention have an inhibitory effect on the mRNA produced by the H4 neuroglioma cells.

TABLE 6

Inhibitory Effect of Triarylmethyl Amine Compounds on H4 Neuroglioma ApoE Production Compared to Housekeeper Genes as Determined by qPCR Analysis.

| Triarylmethyl Amine Compound No. (as listed in Table 1) | ApoE (ng/ml) Cell Count Normalized for Cell Count and Vehicle Treatment | Standard Deviation in Structural Equation Modeling (S/T SEM) |
| --- | --- | --- |
| 6 | 0.48 | 0.15 |
| 22 | 0.48 | 0.03 |
| 33 | 0.59 | 0.04 |

A number of embodiments of the invention have been described. Nevertheless, it will be understood that various modifications may be made without departing from the spirit and scope of the invention. Accordingly, other embodiments are within the scope of the present invention.

What is claimed is:

1. A method for inhibiting expression of apolipoprotein E by mammalian cells comprising:

selecting mammalian cells expressing apolipoprotein E;

contacting said mammalian cells with an effective amount of a triarylmethyl amine compound having general formula (I) in an amount sufficient to at least partially inhibit expression of said apolipoprotein E in said mammalian cells:

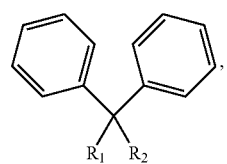

(I)

wherein $R_1$ is formula (II):

(II)

wherein each of $R_3$ and $R_4$ independently is hydrogen, alkyl, substituted alkyl, aryl, substituted aryl, or heterocycle; and $R_2$ is aryl, substituted aryl, or heterocycle.

2. A method according to claim 1, wherein said R1 is a member selected from the group consisting of:

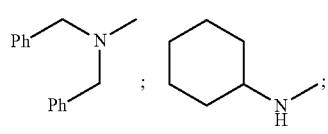

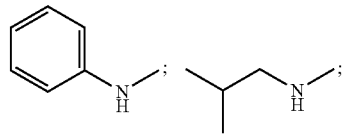

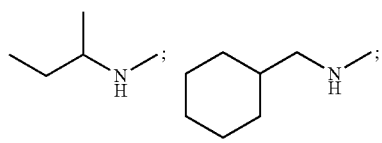

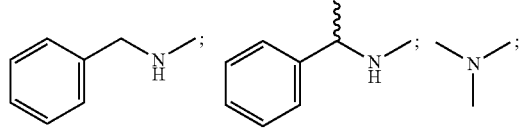

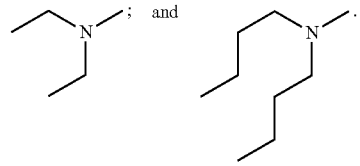

3. A method according to claim 1, wherein said $R_2$ is a member selected from the group consisting of:

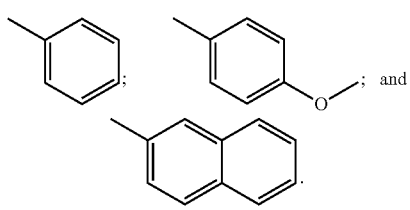

4. A method according to claim 1, wherein said mammalian cells are human cells.

5. A method according to claim 4, wherein said human cells are human brain cells.

6. A method according to claim 1, wherein said $R_1$ is

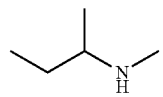

and said $R_2$ is

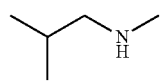

7. A method according to claim 1, wherein said $R_1$ is

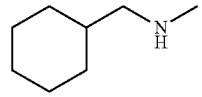

and said $R_2$ is

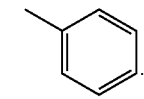

8. A method according to claim 1, wherein said $R_1$ is and said $R_2$ is

* * * * *